United States Patent
Wilkins et al.

(10) Patent No.: US 11,573,202 B2
(45) Date of Patent: Feb. 7, 2023

(54) EVALUATION OF GASEOUS AND SOLID BYPRODUCTS FROM CHEMICAL REACTIONS

(71) Applicant: The United States of America, as represented by the Secretary of the Navy, Crane, IN (US)

(72) Inventors: Benjamin P Wilkins, Jasper, IN (US); Jonathan M Dilger, Bloomington, IN (US); Kelly M Thoreson, Bloomington, IN (US); Brooks P Proctor, Bloomington, IN (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 239 days.

(21) Appl. No.: 17/179,501

(22) Filed: Feb. 19, 2021

(65) Prior Publication Data
US 2022/0268733 A1 Aug. 25, 2022

(51) Int. Cl.
*G01N 25/26* (2006.01)
*G01N 27/626* (2021.01)

(52) U.S. Cl.
CPC .......... *G01N 27/626* (2013.01); *G01N 25/26* (2013.01)

(58) Field of Classification Search
CPC .............. G01N 27/626; G01N 25/26; G01N 2030/067; G01N 2030/126; G01N 30/12; G01N 2030/025; G01N 2030/8845; G01N 33/227; G01N 30/7206; H01J 49/004
USPC ........................................ 250/281, 282, 288
See application file for complete search history.

(56) References Cited

U.S. PATENT DOCUMENTS

2021/0278379 A1* 9/2021 Shibutani .............. G01N 30/30

* cited by examiner

*Primary Examiner* — Michael Maskell
(74) *Attorney, Agent, or Firm* — Naval Surface Warfare Center, Crane Division

(57) ABSTRACT

The invention relates to a method and apparatus for evaluating reaction molecular byproducts of pyrotechnic reactions. A closed calorimetry bomb holds pyrotechnic material, which is detonated by a charge. The calorimetry bomb is vented directly into a gas chromatography machine, where gas phase molecules are separated based on their polarity. The separated molecules are then injected into a mass spectrometer and characterized by their mass fragmentation. The remaining residual solids within the bomb are extracted and injected into a liquid chromatography instrument where they are separated by their polarity. The separated molecules are then injected into a mass spectrometer and characterized by their mass fragmentation pattern. The method provides a complete picture of the reaction pathways and products to aid in regulatory compliance of incorporating energetic materials into real-world applications, particularly those in the family of PFAS containing compositions.

20 Claims, 2 Drawing Sheets

EVALUATION OF GASEOUS AND SOLID BYPRODUCTS FROM CHEMICAL REACTIONS

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon. This invention (Navy Case 210070US01) is assigned to the United States Government and is available for licensing for commercial purposes. Licensing and technical inquiries may be directed to the Technology Transfer Office, Naval Surface Warfare Center Crane, email: Cran_CTO@navy.mil.

FIELD OF THE INVENTION

The field of the invention relates generally to the evaluation of byproducts from chemical reactions. More particularly, it pertains to the use of mass spectrometry-based techniques to identify classes of molecular byproducts of pyrotechnic reactions.

BACKGROUND

Fluorine containing compounds, such as Per- and polyfluoroalkyl substances (PFAS), Perfluorooctane sulfonate (PFOS), perfluorooctanoic acid (PFOA), and other long-chain PFAS are an emerging family of compounds found in many industrial and consumer products. These compounds are recognized by the Environmental Protection Agency (EPA) as being toxic to human health and persistent in the environment. Largely due to their use in fire suppressants, these long-chain PFAS have contaminated thousands of sites. Such contamination has attracted regulatory and citizen attention, which has fueled recent efforts to evaluate the regulation of all types of PFAS. Another area of concern is related to the growing public concern of PFAS contamination from open burning, open detonation (OB/OD) and testing operations on military ranges. Currently, special-interest groups are using unsubstantiated claims regarding PFAS emissions to pressure the EPA to ban OB/OD of polymer-based explosives.

Current methods for the study of reaction byproducts are primarily performed using one of two different methods. The first method involves sampling the open burn/detection and injecting the collected headspace into a gas chromatography/mass spectrometer (GC/MS). The second method uses a direct heating probe connected to GC/MS. The problems inherent with these methods are that open headspace collection results in diluted samples that may allow low concentrations byproducts to be missed or require addition equipment to concentrate sample. Additionally, when a direct heating probe is used, some pyrotechnics burn at a high enough temperature to result in damaged equipment. Furthermore, a direct heating probe only allows for the analysis of anaerobic gases.

SUMMARY OF THE INVENTION

The present invention overcomes the problems inherent with current methods for evaluating pyrotechnic reaction molecular byproducts by using a new and improved method that delivers improved sample quantity, allows for reactions to occur under both anaerobic and aerobic conditions, and allows for hot burning pyrotechnics to be characterized. This is accomplished by using a calorimetry bomb as a closed vessel for combustion and fitting the top of it with a vent that leads directly into the GC/MS. The top of the calorimetry bomb is easily removable, allowing for solid byproduct remains to be collected by solvent extraction and injection in to a UPLC/MS. This method provides a complete picture of the reaction pathways and products to aid in regulatory compliance of incorporating energetic materials into real-world applications.

According to an illustrative embodiment of the present disclosure, the present invention provides a method for evaluating reaction molecular byproducts of pyrotechnic materials.

According to a further illustrative embodiment of the present disclosure, the present invention delivers improved sample quantity and allows for reactions to occur under both anaerobic and aerobic conditions.

According to a final illustrative embodiment of the present disclosure, the present invention allows for hot burning pyrotechnics to be characterized.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Generally, an embodiment of the present invention discloses a method and apparatus for evaluating reaction molecular byproducts. A closed calorimetry bomb holds pyrotechnic material, which is detonated by a charge through a platinum wire. The bomb is then vented directly into a gas chromatography where gas phase molecules are separated based on their polarity. The separated molecules are then injected into a mass spectrometer to be characterized by their mass fragmentation. The remaining residual solids within the bomb are then extracted by using either water or acetonitrile. The dissolved solids are then injected into a liquid chromatography instrument where they are separated by their polarity. The separated molecules are then injected into a mass spectrometer were they are characterized by their mass fragmentation pattern. The method and apparatus described herein allows for reactions to occur under both anaerobic and aerobic conditions, and allows for hot burning pyrotechnics to be characterized. This in turn provides a complete picture of the reaction pathways and products, which can aid in regulatory compliance of incorporating energetic materials into real-world applications, particularly those in the family of PFAS containing compositions.

The method comprises: providing a closed calorimetry bomb; inserting a material within the calorimetry bomb; initiating a charge to detonate the material within the calorimetry bomb, wherein detonation creates gas phase molecules and solids; venting the gas phase molecules from the calorimetry bomb directly into a gas chromatography machine, wherein the gas phase molecules are separated based on polarity; injecting the separated gas phase molecules into a mass spectrometer; characterizing the separated gas phase molecules in the mass spectrometer by their mass fragmentation; extracting the solids within the calorimetry bomb; injecting the solids into a liquid chromatography instrument where they are separated based on polarity; and characterizing the separated solids in the mass spectrometer by their mass fragmentation.

Figure 1:
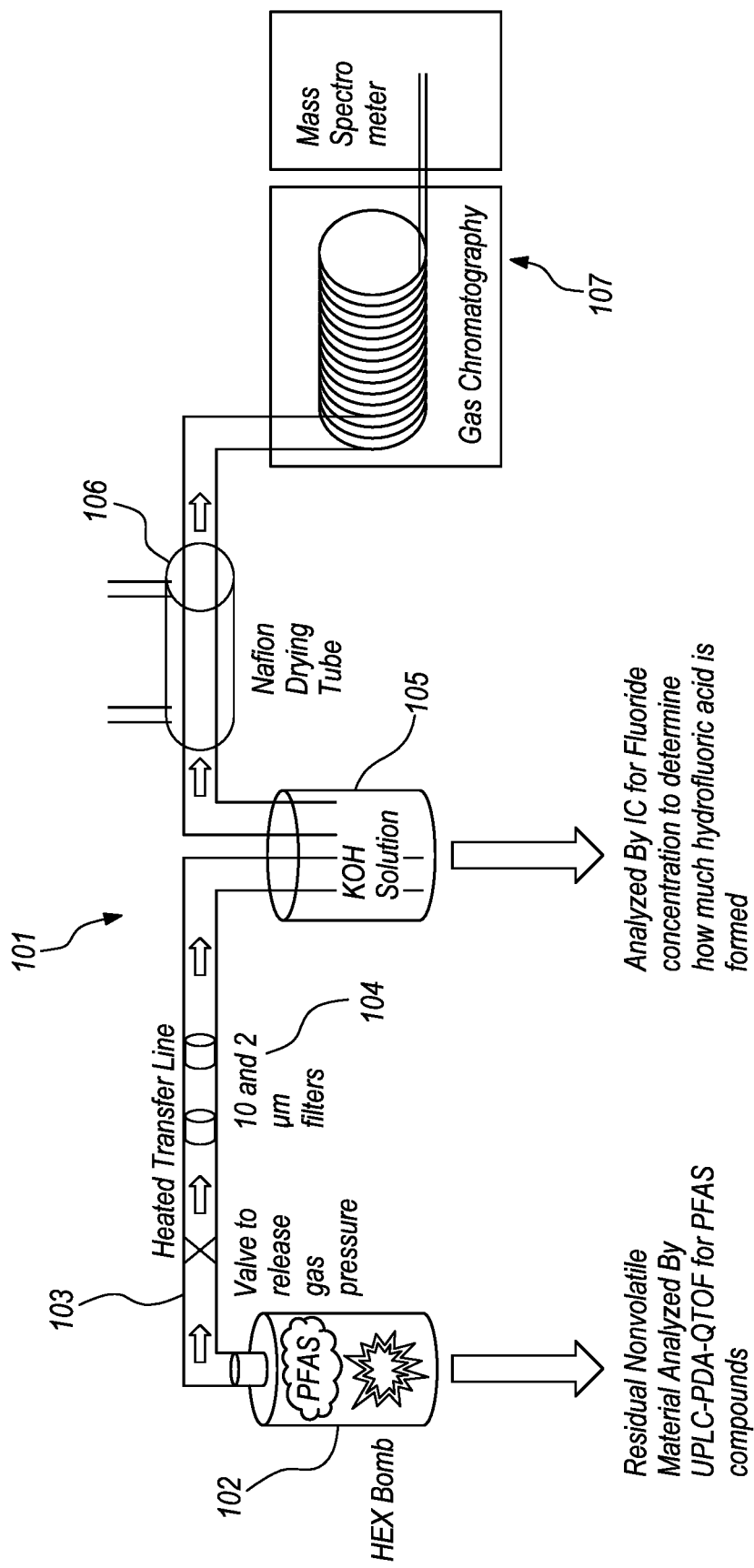
FIG. 1 shows a diagram of the calorimetry bomb set-up for analysis of gas emission by GC/MS from explosive compounds.

Referring now to FIG. 1, there is shown a diagram of the calorimetry bomb set-up 101 for analysis of gas emission by gas chromatography/mass spectrometry (GC/MS) from pyrotechnic or explosive compounds. In this non-limiting example, the present invention will be used for detecting byproducts containing Per- and polyfluoroalkyl substances (PFAS), however, any sample type that can be detonated is contemplated. Samples of either magnesium-Teflon-Viton (MTV) or plastic bonded explosives (PBX) ranging from 1.0 mg to 2.0 g are placed in a closed, constant volume vessel, such as an oxygen bomb calorimeter or a Parr bomb 102. The sample is ignited under both air and inert atmospheres by passing a voltage through a wire, such as a platinum wire 107 that is in direct contact with the sample material. An aliquot of the combustion gases is vented through a valve, such as a Swagelock valve in the top of the Parr bomb 102, and travels through a heated transfer line 103. The gases pass through two particle filters 104, (preferably a 10 and a 2 µm filter) an acid trap 105 (described in more detail below), and a moisture trap 106 (preferably a Nafion drying tube), all of which are contained within the transfer line 103.

In the preferred embodiment, the acid trap 105 is used to detect the amount of hydrofluoric acid produced by detonation. As is well understood, Hydrogen fluoride (HF) is a common byproduct of the combustion of explosives and pyrotechnics that can be used to constrain how Fluoride is partitioned during combustion. To quantify the mass of HF generated during detonation/combustion, a Potassium Hydroxide (KOH) trap is placed in the heated transfer line 103, where it collects combustion gases. The KOH solution neutralizes any HF formed during combustion, thereby putting fluoride into solution. Following a combustion event, such as detonation of the materials within the Par bomb 102, the KOH solution is analyzed by Ion Chromatography (IC) to determine fluoride concentration, which in turn is used to constrain how much fluoride is partitioned into PFAS or other fluorinated byproducts.

From the transfer line 103, the gases are transferred into the GC/MS instrument 107. The GC/MS 107 separates and detects volatile and semi-volatile compounds. The mass spectrum of each compound is then analyzed and interpreted with the aid of a commercially available library of PFAS compounds. Fluorine containing molecules not found within the commercially available PFAS library are preferably indexed in a local library that can then be shared with other Department of Defense (DOD) and national laboratories.

Figure 2:
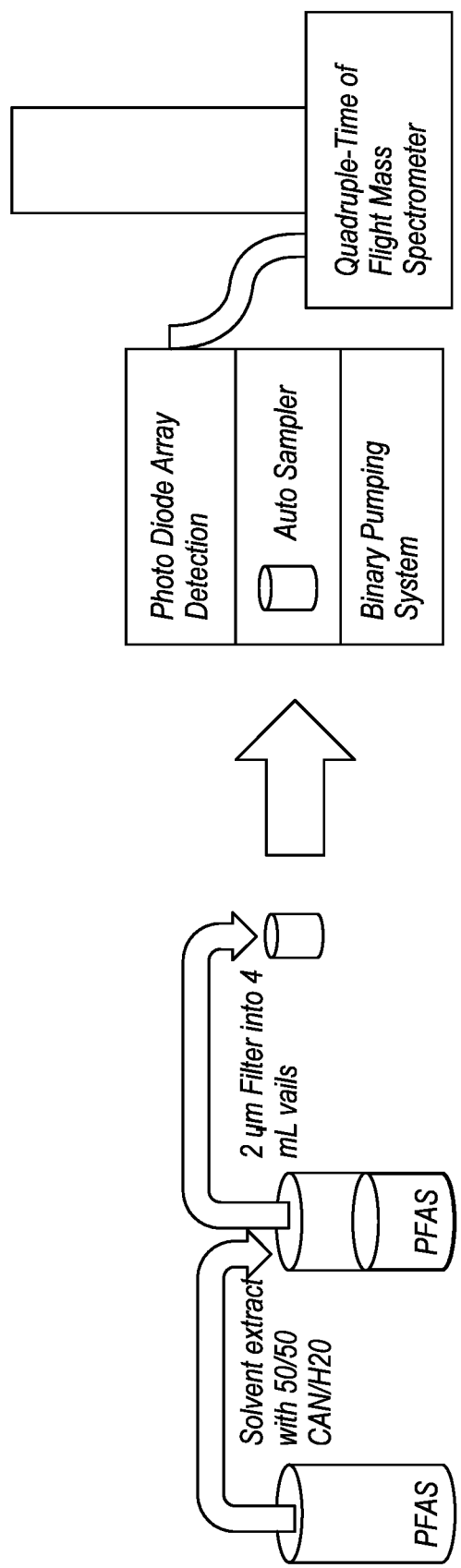
FIG. 2 shows a diagram of the extraction and analysis of materials from post-ignition residuals of explosive compounds.

Referring now to FIG. 2, there is shown a diagram of the extraction and analysis of materials from post-ignition residuals of explosive compounds. After analysis of all gaseous products, the residual solids are removed from the Parr bomb and dissolved with an acetonitrile (ACN) and/or water solvent solution 201. Following extraction, the solution is filtered using a 2 µm nylon or glass microfiber syringe filter 202 and analyzed by mass spectrometry.

In the preferred embodiment, the residual solids are analyzed with an Ultra Performance Liquid Chromatography-Photo Diode Array-Quadrupole-Time of Flight (UPLC-PDA-QTOF) mass spectrometer 203. The separation of different PFAS compounds is performed using the same methodology currently implemented by the EPA (EPA Methods 8328, 533, 8327, and 537/537.1). Molecules separated by Liquid Chromatography (LC) are investigated first by passing the analyte through a nondestructive wideband photo diode array (PDA) detector, and then through a high-resolution Quadrupole-Time of Flight mass spectrometer. These detection systems are preferably arranged in series. Like the GC/MS method described above, the QTOF allows for the identification of unknown molecules not found in the PFAS library via the mass fragmentation spectra of the compound. Any new unindexed mass fragmentation spectrums that contain fluoride will have their molecular structure determined and the local library updated.

The apparatus of the present invention comprises a closed calorimetry bomb, a wire, a transfer line, a first mass spectrometer connected to said gas chromatography machine, a liquid chromatography instrument, a nondestructive wideband photo diode array (PDA) detector, and second mass spectrometer. The wire is used for detonating material within the closed calorimetry bomb, such as MTV or PBX, as described above. The transfer line is fluidly connected to the closed calorimetry bomb at a first end and to a gas chromatography machine at a second end, and includes two particle filters, an acid trap, and a moisture trap. The acid trap comprises a Potassium Hydroxide solution that neutralizes Hydrogen Fluoride formed during combustion, putting Fluoride into solution for analysis by Ion Chromatography to determine Fluoride concentration. In use, the apparatus evaluates reaction molecular byproducts by characterizing gas phase molecules and solids by their mass fragmentation, as described in the method above.

Although the invention has been described in detail with reference to certain preferred embodiments, variations and modifications exist within the spirit and scope of the invention as described and defined in the following claims.

The invention claimed is:
1. A method for evaluating reaction molecular byproducts, comprising:
providing a closed calorimetry bomb;
inserting a material within said calorimetry bomb;
initiating a charge to detonate said material within said calorimetry bomb, wherein detonation creates gas phase molecules and solids;
venting said gas phase molecules from said calorimetry bomb directly into a gas chromatography machine, wherein said gas phase molecules are separated based on polarity;
injecting said separated gas phase molecules into a mass spectrometer;
characterizing said separated gas phase molecules in said mass spectrometer by their mass fragmentation;
extracting said solids within said calorimetry bomb;
injecting said solids into a liquid chromatography instrument where they are separated based on polarity;
injecting said separated solids into a mass spectrometer; and characterizing said separated solids in said mass spectrometer by their mass fragmentation.

2. The method of claim 1, wherein said separated solids are characterized with a nondestructive wideband photo diode array (PDA) detector and a high-resolution Quadrupole-Time of Flight mass spectrometer.

3. The method of claim 1, wherein said material is a pyrotechnic material.

4. The method of claim 1, wherein said solids are extracted from said calorimetry bomb with a liquid.

5. The method of claim 4, wherein said liquid is acetonitrile.

6. The method of claim 5, wherein said liquid is water.

7. The method of claim 1, wherein detonation is performed with a platinum wire.

8. A method for evaluating reaction molecular byproducts, comprising:
providing a closed calorimetry bomb;
inserting a material within said calorimetry bomb;
initiating a charge to detonate said material within said calorimetry bomb, wherein detonation creates gas phase molecules and solids;
venting said gas phase molecules from said calorimetry bomb through a transfer line comprising two particle filters, an acid trap, and a moisture trap, and into a gas chromatography machine, wherein said gas phase molecules are separated based on polarity;
injecting said separated gas phase molecules into a mass spectrometer;
characterizing said separated gas phase molecules in said mass spectrometer by their mass fragmentation;
extracting said solids within said calorimetry bomb;
injecting said solids into a liquid chromatography instrument where they are separated based on polarity; and
characterizing said separated solids by their mass fragmentation with a nondestructive wideband photo diode array (PDA) detector and a high-resolution Quadrupole-Time of Flight mass spectrometer.

9. The method of claim 8, wherein said the acid trap comprises a Potassium Hydroxide solution that neutralizes Hydrogen Fluoride formed during combustion, putting Fluoride into solution for analysis by Ion Chromatography to determine Fluoride concentration.

10. The method of claim 8, wherein material is a pyrotechnic material.

11. The method of claim 8, wherein said solids are extracted from said calorimetry bomb with a liquid.

12. The method of claim 11, wherein said liquid is acetonitrile.

13. The method of claim 11, wherein said liquid is water.

14. The method of claim 8, wherein detonation is performed with a platinum wire.

15. An apparatus for evaluating reaction molecular byproducts, comprising:
a closed calorimetry bomb;
a wire for detonating material within said closed calorimetry bomb;
a transfer line fluidly connected to said closed calorimetry bomb at a first end and to a gas chromatography machine at a second end;
a first mass spectrometer connected to said gas chromatography machine;
a nondestructive wideband photo diode array (PDA) detector and second mass spectrometer;
wherein said apparatus evaluates reaction molecular byproducts by characterizing gas phase molecules and solids by their mass fragmentation.

16. The apparatus of claim 15, wherein said transfer line further comprises two particle filters, an acid trap, and a moisture trap.

17. The apparatus of claim 16, wherein said the acid trap comprises a Potassium Hydroxide solution that neutralizes Hydrogen Fluoride formed during combustion, putting Fluoride into solution for analysis by Ion Chromatography to determine Fluoride concentration.

18. The apparatus of claim 15, wherein said second mass spectrometer comprises a high-resolution Quadrupole-Time of Flight mass spectrometer.

19. The apparatus of claim 15, wherein said wire is a platinum wire.

20. The apparatus of claim 15, further comprising a liquid chromatography instrument coupled to said apparatus for separating said byproducts by their polarity.

* * * * *